US008445840B2

(12) United States Patent
Feke

(10) Patent No.: US 8,445,840 B2
(45) Date of Patent: *May 21, 2013

(54) IMAGING TARGET FOR TESTING QUALITY OF MULTIPLE-MAGNIFICATION FOCUS AND IMAGE CO-REGISTRATION

(75) Inventor: Gilbert Feke, Durham, CT (US)

(73) Assignee: Bruker Biospin Corporation, Billerica, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/235,537

(22) Filed: Sep. 19, 2011

(65) Prior Publication Data

US 2012/0051523 A1 Mar. 1, 2012

Related U.S. Application Data

(63) Continuation of application No. 12/354,830, filed on Jan. 16, 2009, now Pat. No. 8,050,735, and a continuation-in-part of application No. 12/195,452, filed on Aug. 21, 2008, now Pat. No. 8,039,788.

(60) Provisional application No. 60/970,564, filed on Sep. 7, 2007, provisional application No. 61/024,621, filed on Jan. 30, 2008.

(51) Int. Cl.
*G01D 18/00* (2006.01)

(52) U.S. Cl.
USPC .................................. 250/252.1; 378/207

(58) Field of Classification Search
USPC .................................. 250/252.1; 378/207
See application file for complete search history.

(56) References Cited

U.S. PATENT DOCUMENTS

| 4,814,889 | A | 3/1989 | Covey |
| 5,651,046 | A | 7/1997 | Floyd et al. |
| 5,768,443 | A | 6/1998 | Michael et al. |
| 6,231,231 | B1 | 5/2001 | Farrokhnia et al. |
| 6,409,383 | B1 | 6/2002 | Wang et al. |
| 2008/0012006 | A1 | 1/2008 | Bailey et al. |

OTHER PUBLICATIONS

Commonly assigned U.S. Appl. No. 61/024,621, filed Jan. 30, 2008, Feke et al., titled: Apparatus and Method for Multi-Modal Imaging.

*Primary Examiner* — David Porta
*Assistant Examiner* — Carolyn Igyarto
(74) *Attorney, Agent, or Firm* — O'Shea Getz P.C.

(57) ABSTRACT

An imaging target, suited for use in multi-modal imaging systems, includes test patterns for testing quality of focus and co-registration for multiple magnifications and multiple modalities of operation of a multimodal imaging system.

18 Claims, 6 Drawing Sheets

IMAGING TARGET FOR TESTING QUALITY OF MULTIPLE-MAGNIFICATION FOCUS AND IMAGE CO-REGISTRATION

CROSS REFERENCE TO RELATED APPLICATIONS

This is a Continuation-in-Part of U.S. patent application Ser. No. 12/195,452 filed Aug. 21, 2008 now U.S. Pat. No. 8,039,788 by Feke entitled IMAGING TARGET FOR TESTING QUALITY OF MULTIPLE-MAGNIFICATION FOCUS AND IMAGE CO-REGISTRATION, which claimed priority to (a) U.S. Patent Application Ser. No. 60/970,564 filed Sep. 7, 2007 by Feke entitled SELF-ALIGNING MULTIMODAL MULTIPLE-MAGNIFICATION FOCUS AND CO-REGISTRATION TEST PATTERN TARGET; and (b) U.S. Patent Application Ser. No. 61/024,621 filed Jan. 30, 2008 by Feke entitled APPARATUS AND METHOD FOR MULTI-MODAL IMAGING.

This is also a continuation of U.S. patent application Ser. No. 12/354,830 filed Jan. 16, 2009 now U.S. Pat. No. 8,050,735 by Feke entitled APPARATUS AND METHOD FOR MULTI-MODAL IMAGING.

FIELD OF THE INVENTION

The invention relates generally to the field of imaging. Patterns for testing the quality of focus and/or co-registration for multiple magnifications and multiple modalities of operation are within an imaging target that is particularly useful for a multimodal imaging system.

BACKGROUND OF THE INVENTION

In the field of multimodal imaging a single imaging station may be employed to image specimens using multiple imaging modalities. In a multimodal imaging system of the type disclosed in (a) U.S. Pat. No. 7,734,325 by Vizard et al. entitled "APPARATUS AND METHOD FOR MULTI-MODAL IMAGING" and (b) U.S. patent application Ser. No. 12/354,830, previously mentioned, the disclosures of both of which are incorporated herein by reference, a specimen to be imaged may be illuminated by optical back-illumination, optical front-illumination or X-ray back-illumination. The imaging modalities may include bright-field optical imaging at various wavelengths, dark field fluorescence optical imaging at various wavelengths, and radiographic imaging at various energies. There is a need for a simple way for including, in an imaging target, at least one pattern for testing at least one of (a) quality of image focus and (b) quality of image co-registration, for multiple magnifications and multiple modalities of operation of such multimodal imaging systems.

SUMMARY OF THE INVENTION

An imaging target according to an embodiment of the invention is suited for use in a multimodal imaging system. The target may comprise an optically clear, X-ray transparent substrate; at least one pattern formed on the substrate for testing at least one of (a) quality of image focus of one or more modalities of operation of the imaging system for a range of magnifications and illumination wavelengths, and (b) quality of image co-registration of one or more modalities of operation of the imaging system for a range of magnifications and illumination wavelengths. The at least one pattern may be formed from material which is X-ray opaque and either optically reflective or optically absorptive, or both. A second optically clear, X-ray transparent substrate may be included on an opposite side of the at least one pattern from the first substrate, the second substrate being coated with an optically white, X-ray transparent material opposite the at least one pattern. In another embodiment, the at least one pattern may be formed on a first side of the substrate and an optically white, X-ray transparent coating may be formed on a second side of the substrate opposite to the at least one pattern.

BRIEF DESCRIPTION OF THE DRAWINGS

The above and other objects, features, and advantages of the present invention will become more apparent when taken in conjunction with the following description and drawings wherein identical reference numerals have been used, where possible, to designate identical features that are common to the figures.

DETAILED DESCRIPTION OF THE INVENTION

The present invention concerns a device with a target design, which provides a simple solution and method for including, in an imaging target, at least one pattern for testing at least one of (a) quality of image focus and (b) quality of image co-registration, for multiple magnifications and multiple modalities of operation of a multimodal imaging system. The imaging target may be self-aligning in the sense that it includes features such as alignment marks that can be registered with features of an associated imaging system, thus aligning the target to the imaging system. The imaging target according to the invention is useful in a multimodal imaging system that can image objects using bright field, dark field and X-ray imaging modes. Regarding such an imaging system, reference is made to previously mentioned U.S. Pat. No. 7,734,325 and regular U.S. patent application Ser. No. 12/354,830. By using an imaging target or device 1 having a target design 2 as shown in FIGS. 1 to 6, sufficient imaging contrast is achieved so that the imaging target can be used to test at least one of (a) quality of image focus and (b) quality of image co-registration, of multimodal imaging means such as bright-field optical images at various illumination wavelengths, fluorescence optical images at various illumination wavelengths, and radiographic images at various energies.

Figure 1:
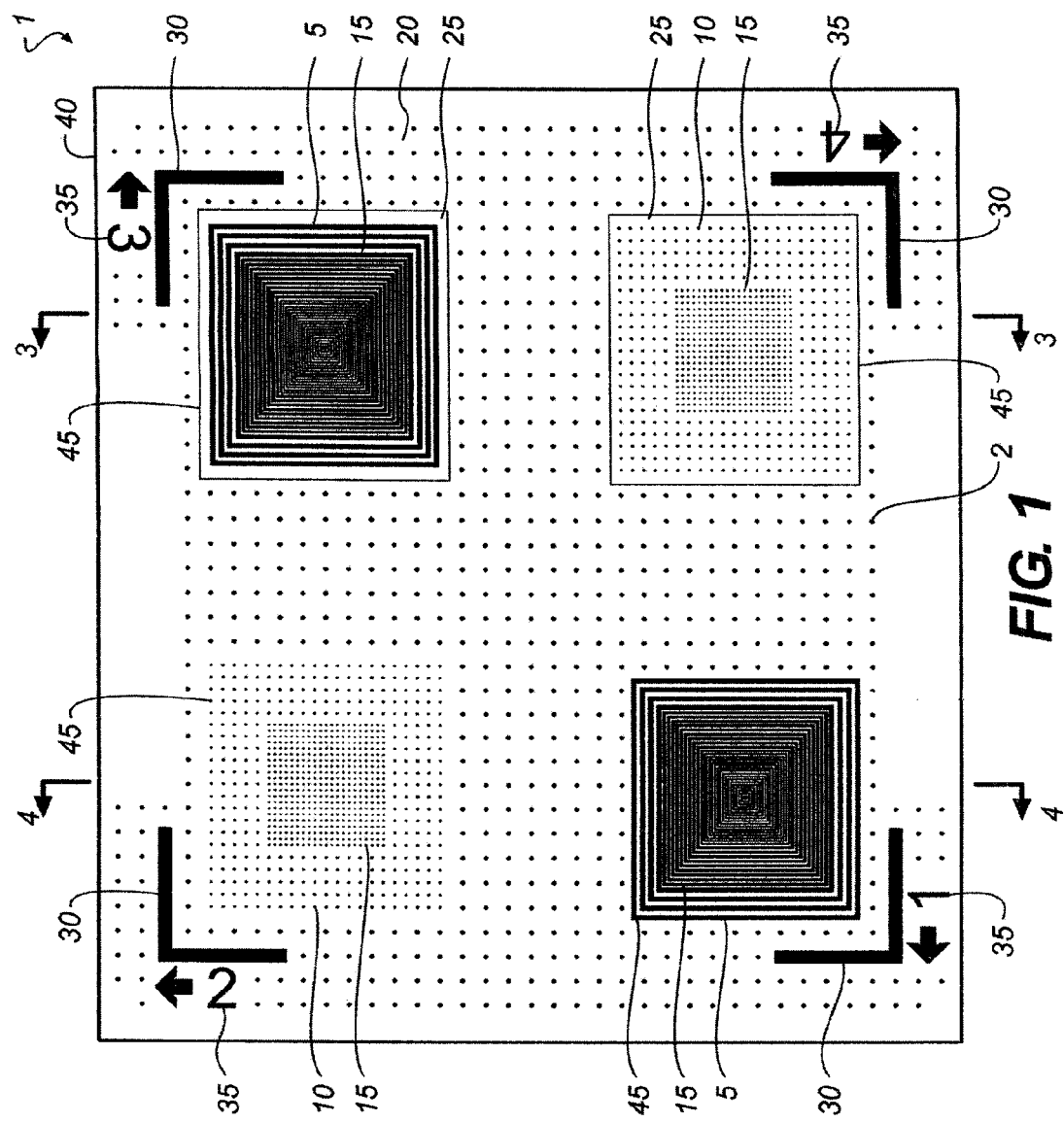
FIG. 1 is a plan view of the front side an imaging target made in accordance with the present invention.
Figure 2:
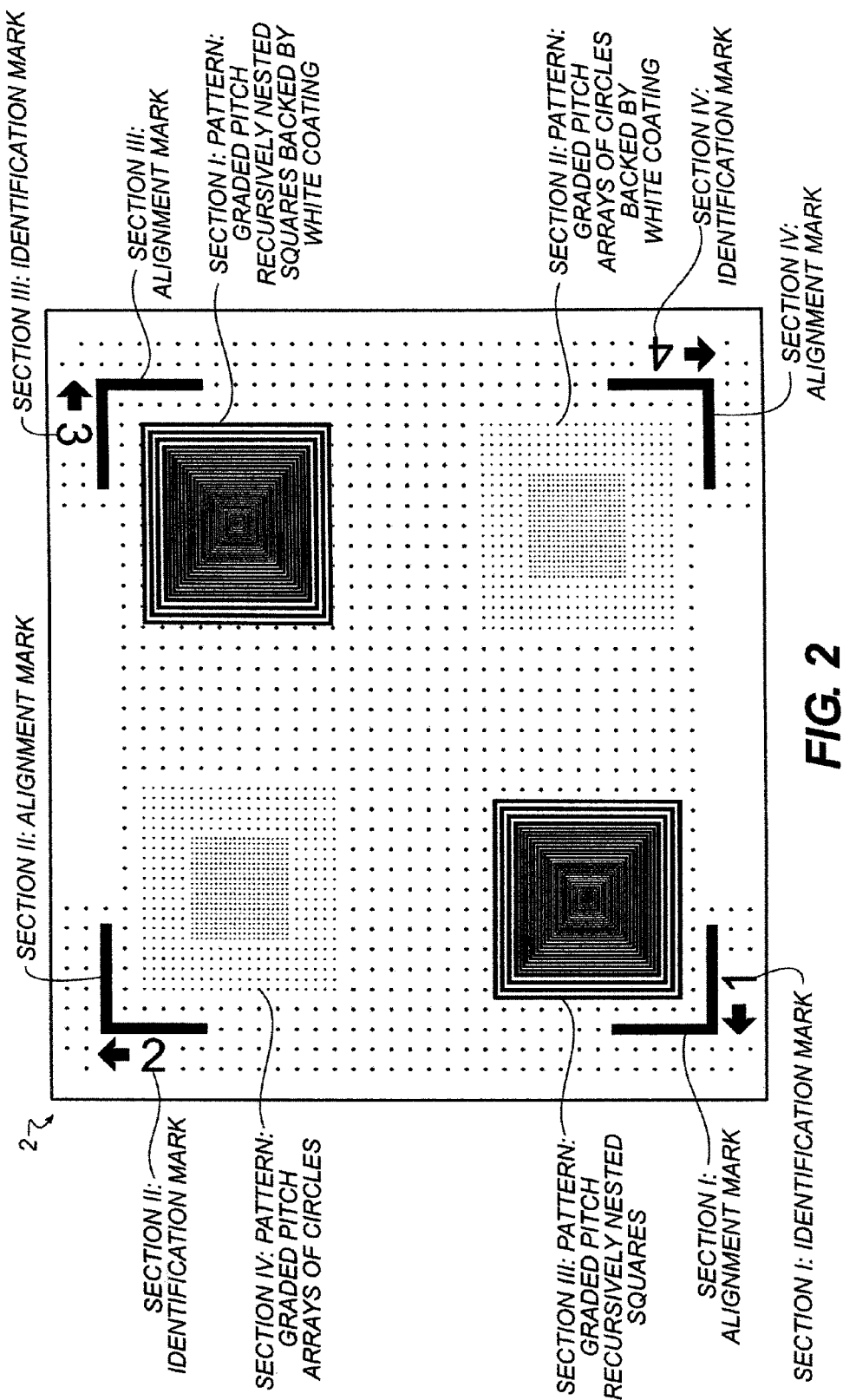
FIG. 2 is a plan view of the front side illustrating in further detail the four sections of target patterns shown in FIG. 1.

Referring to FIGS. 1 to 4, one embodiment of the invention includes a device 1 comprising a target design 2 having one or more sections I, II, III, and IV. Each target design comprises a plurality of layers 15, 20a, 20b and, in sections I and II, layer 25. The target designs further include patterns 5 for testing image focus and 10 for testing image co-registration. In each section patterns are formed on an optically clear, X-ray transparent substrate using known techniques to pattern a material which is X-ray opaque and either optically reflective or optically absorptive, or both, such as chemical etching of a copper film or screen printing of a silver ink. So, in the areas where the patterned material is present, imaging contrast is provided, with respect to the areas of device 1 where patterned material is not present, for at least one, more preferably more than one, and most preferably all of the modalities of operation of the imaging system. In areas of the device surrounding patterns 5 and 10, a background grid pattern of small dots or circles is applied using the same material. The array of dots or circles is useful for testing low magnification configurations of the imaging system. In one actual device as seen in FIGS. 1 and 2, which is useful within a magnification range of at least 0.075 to 0.15 for a system including a square 4 megapixel sensor having 0.8 inch diagonal dimension, these dots are 0.016 inch circles in a 37 by 37 array set at 0.145 inch pitch, with rectangular open spaces for patterns 5 and 10.

Patterns 5 comprise features useful for testing the quality of image focus of at least one, more preferably more than one, and most preferably all of the modalities of operation of the imaging system for a range of magnifications of the imaging system. Patterns 10 are useful for testing the quality of image co-registration among various illumination wavelengths and/or modalities of at least one, more preferably more than one, and most preferably all of the modalities of operation of the imaging system for a range of magnifications of the imaging system.

Referring still to FIGS. 1 to 4, device 1 includes a plurality of alignment features. These features may include patterned alignment features, such as right-angle alignment marks 30 applied at each corner of the device or the physical, rectangular boundary 40 of device 1, or both. The device may have any convenient shape at its boundary. In the illustrated embodiment, patterns 5 and 10 are applied at opposite corners of a device having a rectangular boundary 40. As illustrated, each of patterns 5, 10 may have an essentially rectangular boundary 45. Each set of alignment marks 30 corresponds either to a diagonally opposite pattern of recursively nested geometric figures such as rectangles or squares in pattern 5 or a diagonally opposite graded pitch array of circles in pattern 10. Alignment marks 30, in use, will be registered to physical features of the imaging system. Such as marks or features may be provided at the focal plane of the system, such as on a system platen or a support for an object to be imaged, not illustrated. Each of alignment marks 30 is positioned with respect to a diagonally opposite one of patterns 5, 10 in the corresponding section I to IV. When an alignment mark 30 has been registered to a feature of the imaging system, the center of a selected pattern diagonally opposite the registered alignment mark will be aligned to the center of the field of view of the imaging system. Target design 2 also may include a plurality of identification numerals or marks 35, each mark 35 corresponding to one of sections I to IV and providing information regarding the identity of its respective section.

Within each of boundaries 45, target design 2 comprises a layer 15 with patterned material forming patterns 5, 10 and the background grid pattern of dots or circles previously mentioned, on an optically clear, X-ray transparent substrate 20a. The patterns 5, 10 may be formed from a suitable X-ray opaque metallic material such as copper film or silver ink. The substrate 20a may be formed from optically clear polyester such as Mylar. The patterns formed in layer 15 and substrate 20a provide sufficient imaging contrast so that the patterns of sections I to IV can be used as appropriate to test quality of focus and/or co-registration of bright-field optical images at various illumination wavelengths, fluorescence optical images at various illumination wavelengths, and/or radiographic images at various energies. Test results for quality of focus and/or co-registration of bright-field optical images also may be applied to the dark-field optical imaging mode. A cover substrate 20b of optically clear polyester may be included on opposite side of material 15 from substrate 20a.

Figure 3:
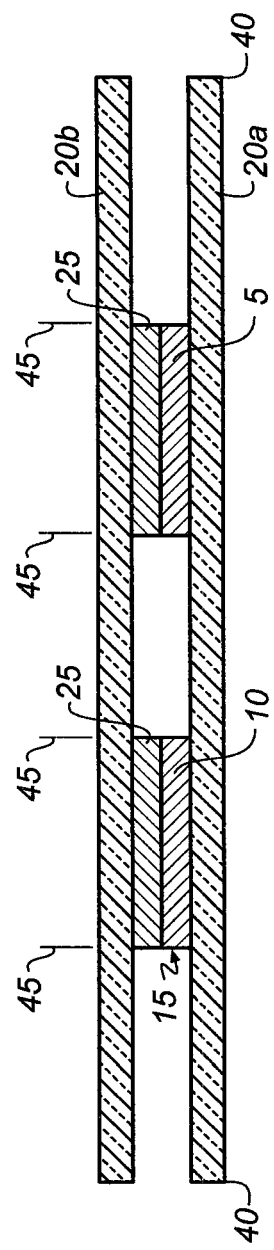
FIG. 3 shows a cross sectional view of the imaging target, taken along line 3-3 of FIG. 1.
Figure 4:
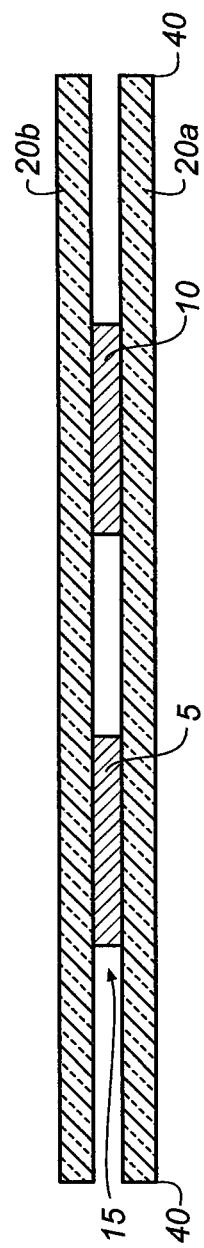
FIG. 4 shows a cross sectional view of the imaging target, taken along line 4-4 of FIG. 1.

As shown in FIG. 3, in sections I and II, patterns 5, 10 are covered by a layer 25 formed on a portion of polyester substrate 20b coated with an optically white, X-ray transparent material. When visible light is passed through from behind the target in a bright-field imaging mode, layer 25 diffuses the back-lighting, thus eliminating the need for any separate external diffuser. Sections I and II also may be used for X-ray imaging mode. As shown in FIG. 3, patterns 5 and 10 include two layers, a portion of layer 15 including a patterned material on substrate 20a; and a layer comprising layer 25 overlying the patterned material. The patterned material, layer 25 and substrate 20a provide sufficient imaging contrast so that sections I and II can be used as appropriate to test quality of focus and/or co-registration of bright-field optical images at various illumination wavelengths, fluorescence optical images at various illumination wavelengths, and/or radiographic images at various energies. As shown in FIG. 4, layer 25 is not provided for patterns 5, 20 in Sections III and IV. Sections III and IV may be used for front-lighting and X-ray imaging mode.

Figure 5B:
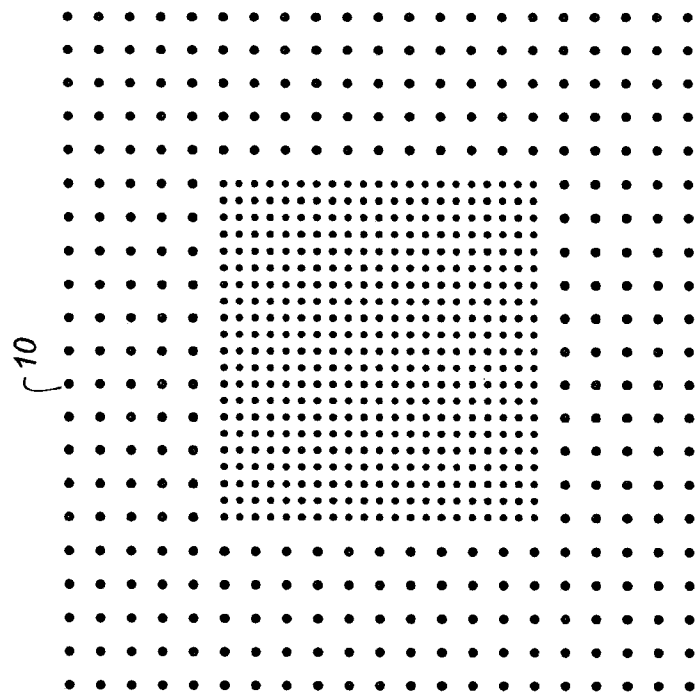
FIGS. 5A and 5B are enlarged schematic plan views of the graded-pitch nested-square pattern and the graded-pitch array of circles pattern in accordance with the present invention.
Figure 5A:
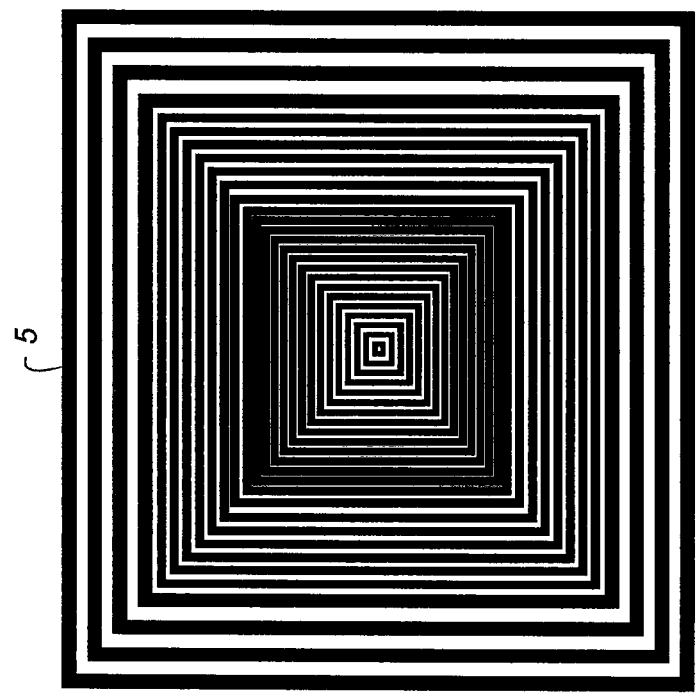

In sections I and III, pattern 5 comprises recursively nested geometric shapes, such as rectangles or the illustrated squares, whereby the center of the pattern may be aligned to the center of the field of view of the imaging system by the physical registration of a corresponding set of alignment features of device 1 to a set of physical features of the imaging system, as previously discussed. The nesting pitch of the geometric shapes is graded to higher pitch and smaller size toward the center of the pattern to provide sufficient pattern content to test imaging system focus quality for multiple magnifications of the imaging system. The line width is equal to half the pitch, as is the spacing between lines. In one actual device as seen in FIG. 5A, which is useful within a magnification range of at least 0.075 to 0.75 for a system including a square 4 megapixel sensor having 0.8 inch diagonal dimension, the pitches are 0.006 inch for 16 nest levels, 0.011 inch for 7 nest levels, 0.016 inch for 8 nest levels, 0.032 inch for eight nest levels and 0.063 inch for 4 nest levels.

In sections II and IV, a pattern 10 comprises a graded pitch array of a shape, such as the illustrated tiny circles, whereby the center of the pattern may be aligned to the center of the field of view of the imaging system by the physical registration of a corresponding set of alignment features of device 1 to a set of physical features of the imaging system, as previously discussed. The graded pitch arrays range in pitch and the circular shapes range in size, whereby the array pitch and shape size are graded to higher pitch and smaller size toward the center of the pattern to provide sufficient pattern content to test quality of co-registration for multiple magnifications of the imaging system. In one actual device as seen in FIG. 5B, which is useful within a magnification range of at least 0.15 to 0.75 for a system including a square 4 megapixel sensor having 0.8 inch diagonal dimension, going out from the center of the array, the pitches are 0.037 inch for a 21 by 21 array of 0.004 inch diameter circles; and 0.071 inch for a 21 by 21 array of 0.008 inch diameter circles.

Figure 6:
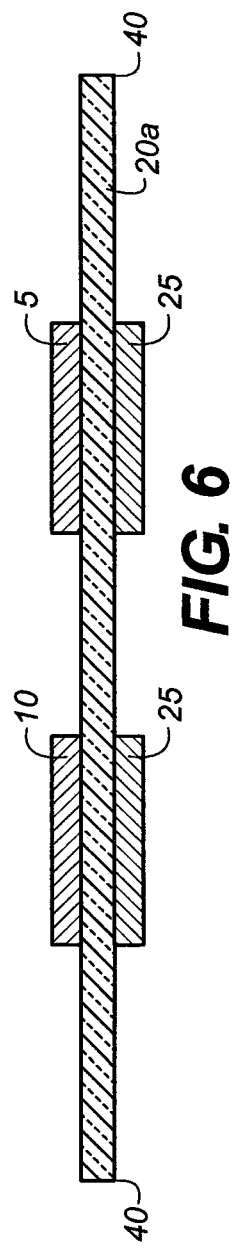
FIG. 6 is a side view of another embodiment of the imaging target in which a single substrate is used.

FIG. 6 shows a side view of an imaging target in which a single polyester substrate 20 has patterns 5 and 10 formed on one side and white coating layers 25 formed on the opposite side, for Sections I and II. Sections III and IV may be formed on either side of substrate 20. This target is somewhat easier to manufacture than that of FIGS. 1 to 4, though its lack of a second protective polyester layer may make it more vulnerable to scratches and wear.

In a first embodiment, a method for use of the target involves steps of: placing the target in the multimodal imaging system; selecting the magnification of interest of the multimodal imaging system; selecting the illumination wavelength or energy for the modality of interest; acquiring one or more images of the target; and evaluating the focus quality of the acquired images. The evaluation of focus quality may be performed using software tools familiar to those skilled in the art.

In a second embodiment, a method for use of the target involves steps of: placing the target in the multimodal imaging system; selecting the magnification of interest of the multimodal imaging system; selecting the illumination wavelength or energy for the modality of interest; acquiring two or more images of the target; and evaluating the co-registration quality of the acquired images. The evaluation of co-registration quality may be performed using software tools familiar to those skilled in the art.

The invention has been described with reference to a preferred embodiment, however, it will be appreciated that variations and modifications can be effected by a person of ordinary skill in the art without departing from the scope of the invention.

What is claimed is:

1. An imaging target for use in a multimodal imaging system, the target comprising:
   an optically clear, X-ray transparent substrate; and
   at least one pattern formed on the substrate for testing at least one of:
   the quality of image focus of one or more modalities of operation of the imaging system for a range of magnifications and illumination wavelengths, and
   the quality of image co-registration of one or more modalities of operation of the imaging system for a range of magnifications and illumination wavelengths,
   wherein the at least one pattern is formed from material which is:
   X-ray opaque, and
   optically reflective or optically absorptive, or both.

2. The imaging target according to claim 1, wherein the at least one pattern comprises:
   at least one layer of the material, the material forming a pattern which provides imaging contrast for one or more of the modalities of operation of an imaging system, with respect to the areas where the patterned material is absent; the pattern comprising features used for testing at least one of the quality of image focus or the quality of image co-registration.

3. The imaging target according to claim 2, further comprising:
   at least one alignment feature positioned corresponding to the at least one pattern for registering the imaging target to a feature of the imaging system to locate the at least one pattern in a field of view of the imaging system; and
   at least one identification mark corresponding to the at least one pattern for providing information regarding the identity of the pattern.

4. The imaging target according to claim 3 wherein the at least one pattern includes:
   a pattern of a recursively nested geometric shapes, the center of the pattern being suited to be aligned to a center of the field of view of the imaging system by the registration of the at least one alignment feature to a feature of the imaging system, and
   the pattern of geometric shapes having a nesting pitch graded to lower pitch toward the center of the pattern to provide sufficient pattern content to test quality of focus for multiple magnifications of the imaging system.

5. The imaging target according to claim 4, wherein the geometric shape is rectangular.

6. The imaging target according to claim 3 wherein the at least one pattern includes:
   a pattern of an array of a geometric shape, the center of the pattern of an array being suited to be aligned to a center of the field of view of the imaging system by the registration of at least one alignment feature to a feature of the imaging system, and
   the array pitch of the geometric shape being graded to lower pitch toward the center of the pattern to provide sufficient pattern content to test imaging system co-registration quality for multiple magnifications of the imaging system.

7. The imaging target according to claim 6, wherein the geometric shape is circular.

8. The imaging target according to claim 1 wherein the modalities of operation of the imaging system include brightfield optical imaging at various wavelengths, fluorescence optical imaging at various wavelengths, and radiographic imaging at various energies.

9. The imaging target according to claim 1 wherein the at least one pattern is formed from a copper film.

10. The imaging target according to claim 1 wherein the at least one pattern is formed from silver ink.

11. The imaging target according to claim 1 wherein the substrate is optically clear polyester.

12. The imaging target according to claim 1, wherein the at least one pattern is formed on a first side of the substrate, further comprising an optically white, X-ray transparent coating formed on a second side of the substrate opposite to the at least one pattern.

13. A method for testing the quality of image focus of an imaging system, the method comprising:
   positioning an imaging target in the multimodal imaging system, the target comprising:
   an optically clear, X-ray transparent substrate; and
   at least one pattern formed on the substrate for testing the quality of image focus of one or more modalities of operation of the imaging system for a range of magnifications,
   wherein the at least one pattern is formed from material which is: (a) X-ray opaque, and (b) optically reflective or optically absorptive, or both;
   selecting a magnification of interest of the multimodal imaging system;
   selecting a modality from the group comprising: optical modality and x-ray modality;
   acquiring one or more images of the target at the selected magnification and selected modality;
   evaluating the acquired images for a focus quality; and
   adjusting the imaging system in response to the focus quality.

14. The method of claim 13 wherein the imaging target comprises two patterns.

15. A method for testing the quality of image focus of an imaging system, the method comprising:
   positioning an imaging target in the multimodal imaging system, the target comprising:
   an optically clear, X-ray transparent substrate; and
   at least one pattern formed on the substrate for testing the quality of image co-registration of two modalities of operation of the imaging system for a range of magnifications, wherein the at least one pattern is formed from material which is: (a) X-ray opaque, and (b) optically reflective or optically absorptive, or both;
selecting a field of view of the multimodal imaging system;
selecting a first modality from the group comprising: optical modality and x-ray modality;
acquiring one or more images of the target at the selected magnification and first modality;
selecting a second modality different from the first modality;
acquiring one or more images of the target at the selected magnification and second modality;
evaluating the acquired images for a focus quality; and
adjusting the imaging system in response to the focus quality.

16. The method of claim 15 wherein the imaging target comprises two patterns.

17. A method for testing the quality of image co-registration of an imaging system, the method comprising:
placing an imaging target in the multimodal imaging system, the target comprising:
an optically clear, X-ray transparent substrate; and
at least one pattern formed on the substrate for testing the quality of image co-registration of one or more modalities of operation of the imaging system for a range of magnifications and illumination wavelengths,
wherein the at least one pattern is formed from material which is: (a) X-ray opaque, and (b) optically reflective or optically absorptive, or both;
selecting a magnification of interest of the multimodal imaging system;
selecting the illumination wavelength or energy for the modality of interest;
acquiring two or more images of the target;
evaluating the co-registration quality of the acquired images; and
adjusting the imaging system in response to the co-registration quality.

18. The method of claim 17 wherein the imaging target comprises two patterns.

* * * * *